US010052154B2

(12) United States Patent
Rephaeli et al.

(10) Patent No.: US 10,052,154 B2
(45) Date of Patent: Aug. 21, 2018

(54) SYSTEM AND METHOD FOR FLUORESCENCE-BASED LASER ABLATION

(71) Applicant: Verily Life Sciences LLC, Mountain View, CA (US)

(72) Inventors: Eden Rephaeli, Menlo Park, CA (US); Chia-Jean Wang, Palo Alto, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 678 days.

(21) Appl. No.: 14/503,706

(22) Filed: Oct. 1, 2014

(65) Prior Publication Data

US 2016/0095661 A1   Apr. 7, 2016

(51) Int. Cl.
*A61B 18/22* (2006.01)
*A61B 5/00* (2006.01)
(Continued)

(52) U.S. Cl.
CPC .............. *A61B 18/22* (2013.01); *A61B 1/043* (2013.01); *A61B 5/0071* (2013.01);
(Continued)

(58) Field of Classification Search
CPC ... A61B 18/22; A61B 18/203; A61B 19/5212; A61B 19/5225; A61B 2018/00577;
(Continued)

(56) References Cited

U.S. PATENT DOCUMENTS 5,951,543 A * 9/1999 Brauer ................. A61B 18/201
606/10
8,160,680 B2   4/2012 Boyden et al.
(Continued)

FOREIGN PATENT DOCUMENTS

JP   2011-75513 A   4/2011
JP   2012-108491 A   6/2012
(Continued)

OTHER PUBLICATIONS

International Search Report, Application No. PCT/US2015/053232, dated Dec. 23, 2015.
(Continued)

*Primary Examiner* — Gary Jackson
*Assistant Examiner* — Zahed Kabir
(74) *Attorney, Agent, or Firm* — McDonnell Boehnen Hulbert & Berghoff LLP

(57) ABSTRACT

In an embodiment, an apparatus and method are described for ablating tissue in response to determining a fluorescence condition. An excitation light source may produce excitation light at a excitation wavelength of a fluorophore. A beam scanner may direct the excitation light towards a tissue location. A fluorophore may produce emission light in response to absorbing the excitation light. A camera may capture an image of the tissue location. In response to the image indicating emission light at the tissue location, an ablation light source may produce ablation light. The beam scanner may direct the ablation light towards the tissue location. Additionally or alternatively, a topography map may be generated and certain aspects of the apparatus and/or the method may be adjusted based on the topography map.

20 Claims, 7 Drawing Sheets

(51) Int. Cl.
*A61B 1/04* (2006.01)
*A61B 19/00* (2006.01)
*A61B 18/20* (2006.01)
*A61B 18/00* (2006.01)
*G02B 26/10* (2006.01)
*G02B 27/14* (2006.01)

(52) U.S. Cl.
CPC .......... *A61B 5/4836* (2013.01); *A61B 18/203* (2013.01); *A61B 19/5212* (2013.01); *A61B 19/5225* (2013.01); *A61B 2018/00577* (2013.01); *A61B 2018/00642* (2013.01); *A61B 2018/00779* (2013.01); *A61B 2018/00904* (2013.01); *A61B 2018/20359* (2017.05); *A61B 2019/5214* (2013.01); *A61B 2019/5231* (2013.01); *A61B 2019/5238* (2013.01); *G02B 26/105* (2013.01); *G02B 27/141* (2013.01)

(58) Field of Classification Search
CPC .......... A61B 2018/00642; A61B 2018/00779; A61B 2018/00904; A61B 2018/2095; A61B 2018/2266; A61B 2019/5214; A61B 2019/5231; A61B 2019/5238; A61B 5/0071; G02B 26/105
USPC .......................................................... 606/3
See application file for complete search history.

(56) References Cited

U.S. PATENT DOCUMENTS

| | | | |
|---|---|---|---|
| 8,285,367 B2 | 10/2012 | Hyde et al. | |
| 8,686,363 B1 * | 4/2014 | Timlin | G02B 21/0032 250/339.07 |
| 8,722,357 B2 | 5/2014 | Baer et al. | |
| 9,116,354 B2 | 8/2015 | Knebel et al. | |
| 2006/0241577 A1 | 10/2006 | Balbierz et al. | |
| 2008/0052052 A1 * | 2/2008 | Stearns | A61B 5/0059 703/6 |
| 2008/0103390 A1 * | 5/2008 | Contag | G01N 21/6428 600/427 |
| 2009/0292211 A1 | 11/2009 | Lin | |
| 2012/0326055 A1 * | 12/2012 | Wilson | A61B 5/0059 250/459.1 |
| 2013/0190742 A1 * | 7/2013 | Connors | A61B 18/20 606/17 |
| 2014/0080087 A1 | 3/2014 | Monty | |
| 2014/0187879 A1 | 7/2014 | Wood et al. | |
| 2014/0187931 A1 * | 7/2014 | Wood | A61B 5/0071 600/431 |
| 2014/0207129 A1 * | 7/2014 | Lee | A61B 18/02 606/12 |
| 2016/0278678 A1 * | 9/2016 | Valdes | A61B 5/14556 |

FOREIGN PATENT DOCUMENTS

| | | |
|---|---|---|
| WO | 2014118782 A2 | 7/2014 |
| WO | 2014/130736 | 8/2014 |

OTHER PUBLICATIONS

Supplementary European Search Report, European Application No. 15845896.8, dated Mar. 9, 2018.

* cited by examiner

SYSTEM AND METHOD FOR FLUORESCENCE-BASED LASER ABLATION

BACKGROUND

Cancer is one of the leading causes of death worldwide. Specifically, breast cancer is the most common cancer type for women, for whom it is either the $1^{st}$ or $2^{nd}$ leading cause of death, depending on ethnicity.

In recent years, one promising approach to real-time detection of breast cancer tumors has involved the use of special markers. These markers can selectively bind to cancer cells, and upon suitable light excitation will fluoresce (emit light), thus providing the surgeon a real-time real-space image of the tumor and its margins. The markers are typically in the red or near infrared wavelength range to avoid tissue autofluorescence in the visible range and have increased depth penetration. However, there is currently no system solution enabling robust and rapid real-time detection of breast cancer tumors using fluorescent markers.

Meanwhile, the use of lasers in the medical theater has been steadily increasing over time. Specifically, the use of lasers to ablate tumors has been explored in various surgical procedures. Lasers can be delivered to the surgical site via articulated arms or specialty fibers. However, the use of both an ablation laser and a simultaneous fluorescent detection scheme would require the operation of two sensitive devices which are required to reference the same coordinate system, thus complicating surgery and depriving surgeons of much-needed dexterity.

SUMMARY

In a first aspect, an apparatus is provided. The apparatus includes an excitation light source, an ablation light source, and a beam combiner. The excitation light source is configured to produce excitation light. The excitation light includes light having a wavelength that corresponds to an excitation wavelength of a fluorophore. The fluorophore is configured to emit emission light at an emission wavelength in response to receiving light at the excitation wavelength. The ablation light source is configured to produce ablation light. The ablation light is configured to ablate tissue. The beam combiner is optically coupled to the excitation light source and the ablation light source. The apparatus also includes a controller. The controller includes a computer programmed to carry out instructions. The instructions include causing the excitation light source to produce excitation light and causing the ablation light source to produce ablation light.

In a second aspect, a method is provided. The method includes causing an excitation light source to produce excitation light. The excitation light includes light having a wavelength that corresponds to an excitation wavelength of a fluorophore. The fluorophore is configured to emit emission light at an emission wavelength in response to receiving light at the excitation wavelength. The method further includes causing a beam scanner to direct the excitation light towards a particular tissue location. The beam scanner is operable to direct the excitation light toward any of a plurality of tissue locations. The method also includes causing a camera to capture an image of at least the particular tissue locations. The camera is configured to detect the emission light emitted by the fluorophore. The method additionally includes determining a fluorescence condition based on the image indicating emission light at the emission wavelength at the particular tissue location. The method further includes responsive to the fluorescence condition, causing an ablation light source to produce ablation light and causing the beam scanner to direct the ablation light towards the particular tissue location. The ablation light source and the excitation light source are optically coupled to the beam combiner and the beam combiner is optically coupled to the beam scanner.

In a third aspect, a method is provided. The method includes determining a topographical map based on a location of a camera, a location of an exit aperture of a beam scanner, and an angle of excitation light with respect to a particular tissue location. The method also includes determining a focal distance to the particular tissue location based on the topographical map. The method additionally includes causing an excitation light source to produce excitation light. The excitation light includes light having a wavelength that corresponds to an excitation wavelength of a fluorophore. The fluorophore is configured to emit emission light at an emission wavelength in response to receiving light at the excitation wavelength. The method further includes causing a beam scanner to direct the excitation light towards a particular tissue location. The beam scanner is operable to direct the excitation light toward any of a plurality of tissue locations. The method yet further includes causing a camera to capture an image of at least the particular tissue location. The camera is configured to detect the emission light emitted by the fluorophore. The method also includes determining a fluorescence condition based on the image indicating emission light at the emission wavelength at the particular tissue location. The method additionally includes, responsive to the fluorescence condition, causing an ablation light source to produce ablation light and causing the beam scanner to direct the ablation light towards the particular tissue location based at least on the focal distance to the particular tissue location. The ablation light source and the excitation light source are optically coupled to a beam combiner and the beam combiner is optically coupled to the beam scanner.

Other aspects, embodiments, and implementations will become apparent to those of ordinary skill in the art by reading the following detailed description, with reference where appropriate to the accompanying drawings.

DETAILED DESCRIPTION

Figure 1A:
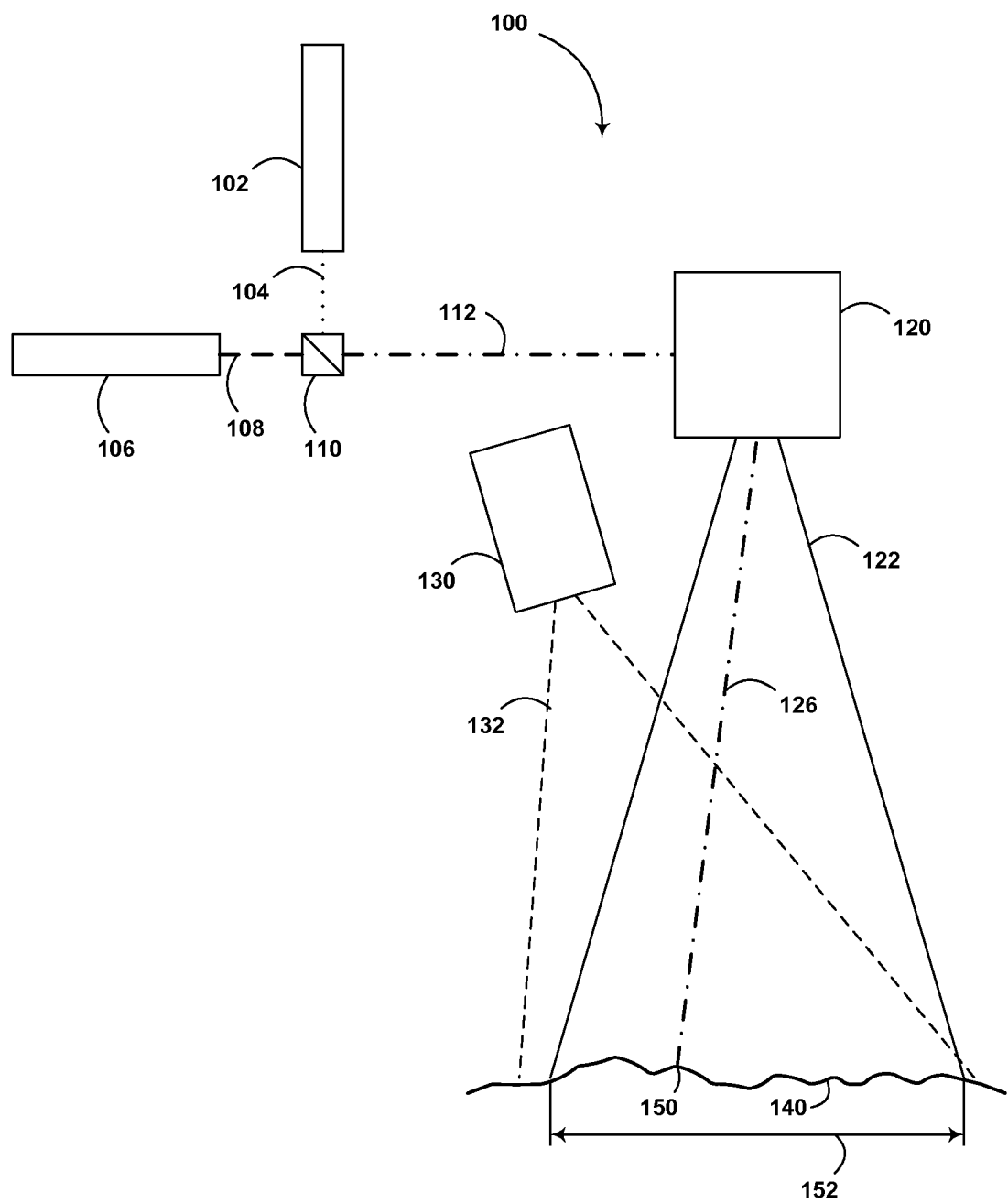
FIG. 1A illustrates an apparatus, according to an example embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where selective ablation of tissue is desired. The environment may include any living or non-living body or a portion thereof. The environment may include non-human tissues. For example, one of skill in the art will recognize that the embodiments disclosed herein may be applied generally to selectively ablate tissue in response to determination of a fluorescence condition in many different contexts. Moreover, while the present disclosure describes embodiments for use in vivo, one of skill in the art will also recognize that in vitro applications are possible as well.

Overview

In an embodiment, an apparatus and a method for its use may include a medical device that can illuminate a tissue location with excitation light from an excitation light source. In response to detecting light at an emission wavelength (e.g. from a fluorophore) at the tissue location, the medical device may cause an ablation light source to produce ablation light so as to ablate tissue at the tissue location. In some embodiments, the device and methods for its use may help to improve selective removal of specific tissue, such as cancerous tissues.

The excitation light source may be configured to produce the excitation light at a wavelength corresponding to an excitation wavelength of a fluorophore. Furthermore, the fluorophore may be configured to emit the emission light in response to receiving and/or absorbing the excitation light. The excitation light source may be a laser (e.g. HeNe) or a light-emitting diode (LED).

The ablation light source may be a mid-infrared wavelength laser, such as a carbon dioxide ($CO_2$) or an argon ion laser. Other light sources and/or lasers configured to remove tissue by ablation are considered within the context of this disclosure.

The ablation light source and the excitation light source may be optically coupled to a beam combiner. The beam combiner may include a dichroic material configured to reflect either of the ablation light or the excitation light and transmit the other light. The beam combiner may take other forms. For instance, the beam combiner may include a fiber optic y-coupler or other devices configured to combine two beams of light.

A beam scanner may be optically coupled to the beam combiner. The beam scanner may be configured to direct the excitation light and the ablation light towards one or more tissue locations. For example, the beam scanner may include an X-Y mirror galvanometer or other devices operable to direct the excitation light and the ablation light toward any of a plurality of tissue locations.

A camera may be configured to capture an image of at least a particular tissue location illuminated by the excitation light. Furthermore, the camera may be configured to detect light at the emission wavelength. In other words, the camera may be able to detect emission light from the fluorophore or from another source.

The apparatus may include a controller configured to control some or all of the aforementioned elements of the medical device. Specifically, the controller may be configured to cause the excitation light source to produce the excitation light, cause the beam scanner to direct the excitation light towards a particular tissue location, and cause the camera to capture one or more images of at least the particular tissue location. Furthermore, the controller may be configured to determine a fluorescence condition based on the image indicating emission light at the emission wavelength at the particular tissue location. In response to the fluorescence condition, the controller may also cause the ablation light source to produce ablation light and cause the beam scanner to direct the ablation light towards the particular tissue location.

The controller may include a computer having a processor and a memory. The controller may take other forms as well. For example, the controller may include a distributed computing system or a cloud-based server network. Alternatively or additionally, the controller may be a mobile device. The controller may include software, such as hardware drivers and/or application programming interfaces, configured to control the aforementioned elements of the apparatus. The controller may communicate with and/or control some or all of the other elements of the apparatus using wireless communications.

Apparatus Examples

FIG. 1A illustrates an apparatus 100, according to an embodiment. The apparatus 100 may include an excitation light source 102. The excitation light source 102 may be configured to produce excitation light 104. The excitation light source 102 may include a laser, such as a helium neon (HeNe) laser. Alternatively, the excitation light source 102 may be a xenon or mercury lamp, a light emitting diode, or another light source configured to excite a fluorescence property of a fluorophore. In other words, the excitation light source 102 may produce excitation light 104, which may in turn include light having a wavelength that corresponds to an excitation wavelength of a fluorophore. The excitation light 104 may include, but is not limited to, light with wavelength range between 380 nanometers and 1.4 microns.

Fluorophores may absorb light of a particular wavelength and re-emit light at a longer emission wavelength as emission light. As contemplated herein, fluorophores may have excitation wavelengths in the red to near infrared wavelengths, but other excitation wavelengths are possible. The fluorophores may have corresponding emission wavelengths in the visible to near-infrared spectrum, but other emission wavelengths are possible. Some examples of fluorophore molecules include cell/tissue dyes, the active agent of which may include a small molecule, protein, or quantum dot. Some embodiments may involve Förster resonance energy transfer (FRET), in which an excited electron of a first fluorophore (e.g. a donor dye) is passed to a second fluorophore (e.g. an acceptor dye), which may result in a reduced fluorescence. The fluorophore may be incorporated in the tissue 140. Additionally or alternatively, more than one fluorophore may be incorporated into the tissue 140 and/or another fluorophore may be incorporated into other parts of the body, such as surrounding tissue, bone, body cavity, etc. Other combinations of fluorophores are possible and contemplated herein.

Although this disclosure specifically addresses the use of fluorophores as indicating whether to ablate particular tissue locations, other types of luminescence properties may be utilized for such purposes. For example, chemiluminescence and phosphorescence of tissues and various biomarkers may be utilized in association with the methods and devices disclosed herein.

The apparatus 100 further includes an ablation light source 106. The ablation light source 106 may be a laser configured to produce ablation light 108 including a mid-infrared wavelength, such as a carbon dioxide ($CO_2$) laser. Alternatively, the ablation light source 106 may be another type of light source. Ablation light 108 may be configured so as to ablate tissue. That is, the power, duty cycle, repetition rate, spectral characteristics, and focus spot of the ablation light 108 may be configured and/or adjusted so as to remove tissue. The ablation light 108 may include, but is not limited to, the wavelength range between 1.4 microns and 12 microns.

A beam combiner 110 may be optically coupled to the excitation light source 102 and the ablation light source 106. The beam combiner 110 may include a dichroic beam cube/combiner. Alternatively, the beam combiner 110 may include a fiber optic y-coupler or another method of combining two light sources in a collinear fashion. The beam combiner 110 may optionally direct combined light 112 towards a beam scanner 120. FIG. 1A illustrates combined light 112 as including both excitation light 104 and ablation light 108. However, in some embodiments, combined light 112 may further represent either excitation light 104 or ablation light 108. That is, combined light 112 serves to illustrate a substantially collinear path for excitation light 104 and ablation light 108. Some embodiments include the light sources producing light at different times. Additionally or alternatively, embodiments may include the light sources producing light at the same time for at least some portion of a given duty cycle or period of operation.

As shown, the optional beam scanner 120 directs incident light 126 towards a particular tissue location 150. Incident light 126 can include excitation light 104 and/or ablation light 108. Further, the beam scanner 120 has a deflection range 122 within which it can direct incident light 126 towards any of a plurality of tissue locations 152. As described above, incident light 126 serves to show the substantially collinear path of excitation light 104 and ablation light 108, and should not imply that both light sources must produce light at the same time, although such scenarios are contemplated in some embodiments. The beam scanner 120 may include a dual galvanometer operable to deflect the excitation light 104 and the ablation light 108 within the deflection range 122. The deflection range 122 may encompass an area of tissue that includes the plurality of tissue locations 152.

The apparatus 100 may optionally include a camera 130 configured to detect light at least at the emission wavelength. Camera 130 may include a field of view 132. The field of view 132 of camera 130 includes at least the particular tissue location 150 and may encompass all of, or a portion of, the plurality of tissue locations 152, as well as other tissue locations. Alternatively, field of view 132 may include more or less of the deflection range 122. The camera 130 may be a charge-coupled device (CCD) camera or another type of camera configured to capture images of the field of view 132 so as to identify fluorophores emitting emission light at the emission wavelength and/or to help determine the topography of the field of view 132. The camera 130 may be configured to detect light at only near the emission wavelength. Alternatively, the camera 130 may be configured to detect light within a relatively broad wavelength spectrum that encompasses the emission wavelength.

Figure 1B:
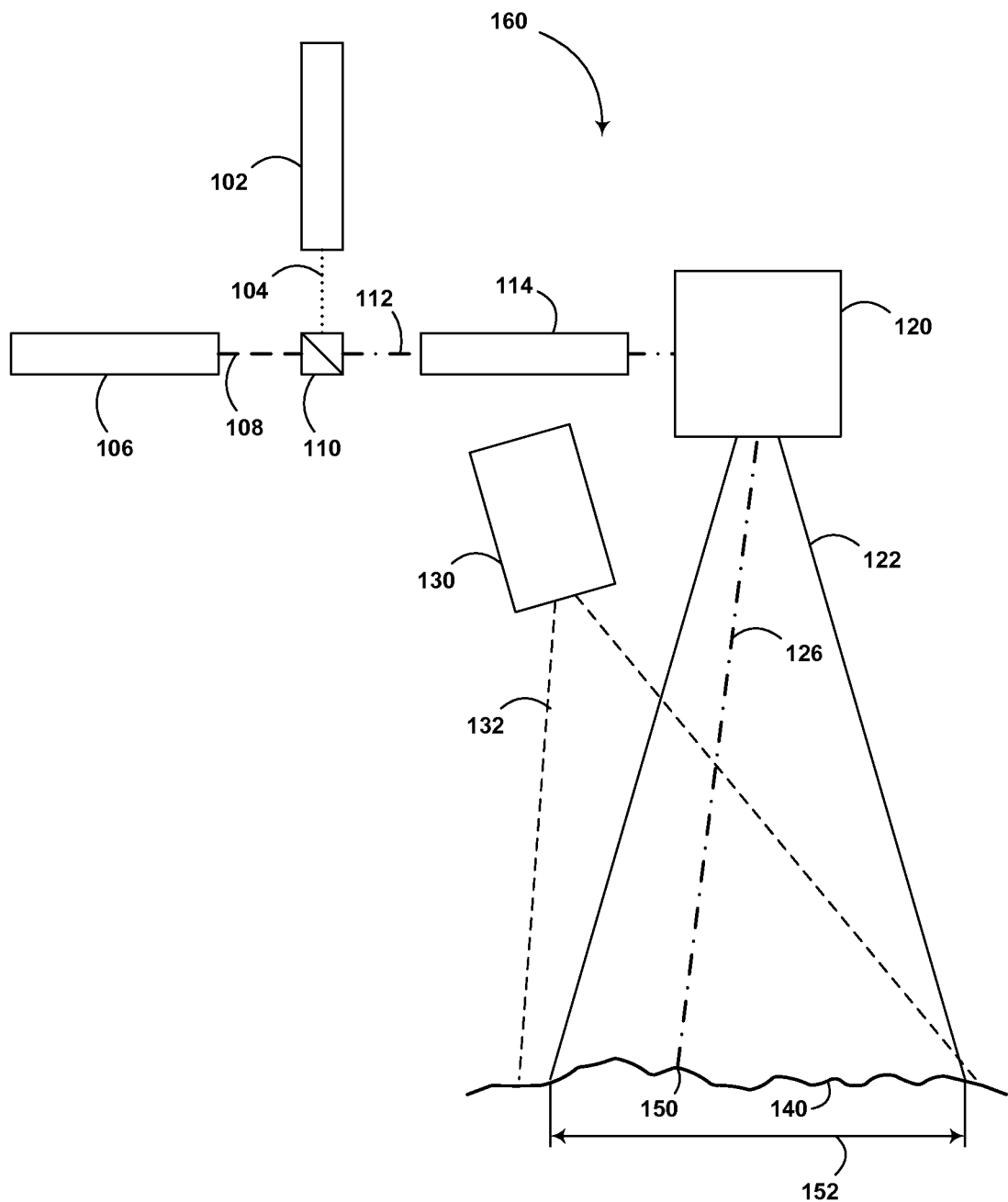
FIG. 1B illustrates an apparatus, according to an example embodiment.

FIG. 1B illustrates an apparatus 160 similar to apparatus 100, but which further includes a beam delivery system 114. The beam delivery system 114 may be optically coupled to the beam combiner 110 and the beam scanner 120. The beam delivery system 114 may include an articulated arm with optics configured to direct the combined light 112 towards the beam scanner 120. For example, the articulated arm may include mirrors and/or other optical components that could direct light from an input of the articulated arm (e.g. fiber optic coupler/s that may accept light) to an output of the articulated arm (e.g. at or near a tissue location). Alternatively, the beam delivery system 114 may include an optical fiber. In some embodiments, the optical fiber may include sapphire or another material configured to transmit both the excitation light 104 and the ablation light 108. The optical fiber may be a multimode optical fiber.

Figure 1C:
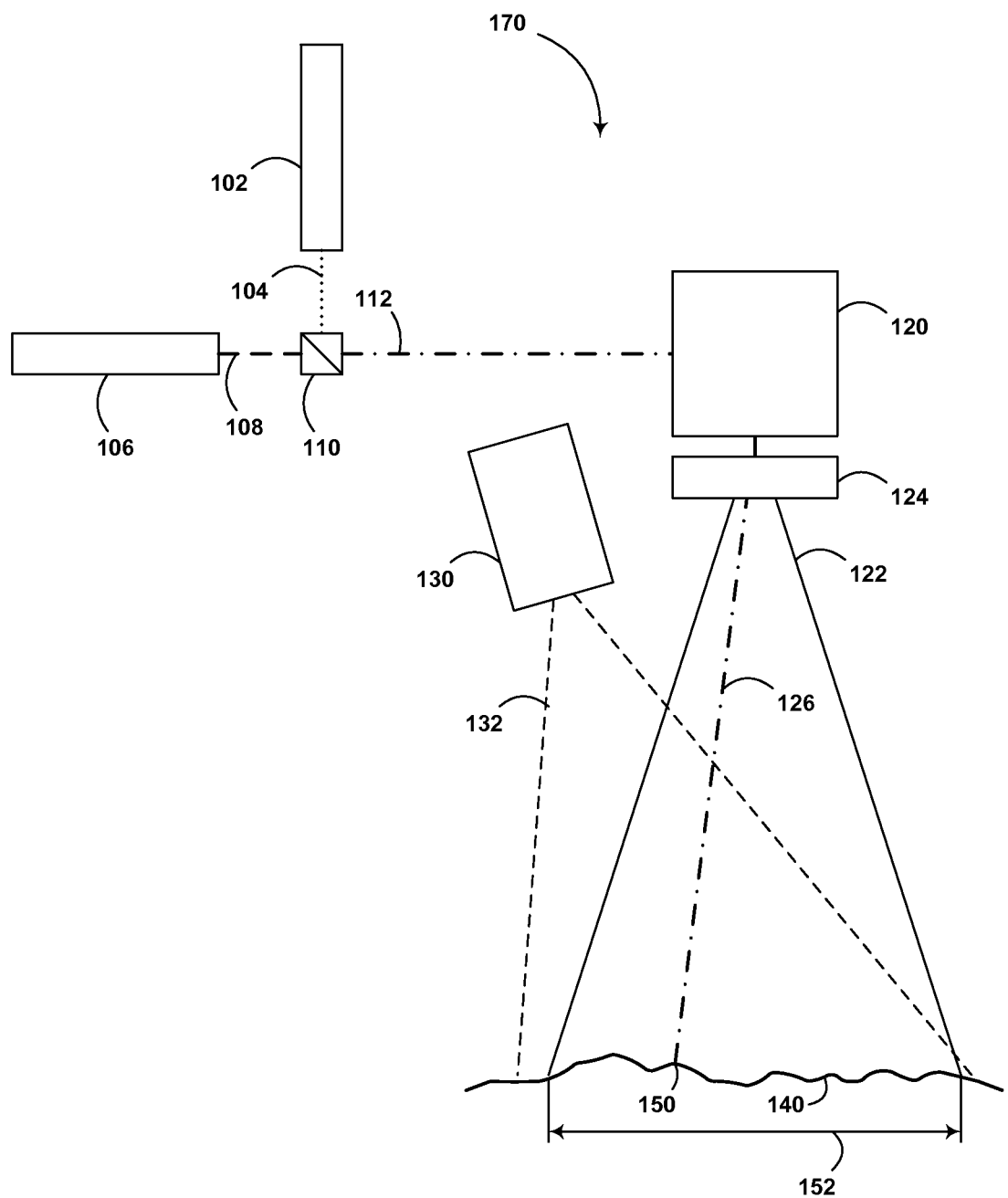
FIG. 1C illustrates an apparatus, according to an example embodiment.

FIG. 1C illustrates an apparatus 170 similar to apparatus 100, but which further includes an optical system 124. The optical system 124 may be optically coupled to the beam scanner 120 and/or other elements of apparatus 170. The optical system 124 may include elements such as a lens and an exit aperture. Other elements of optical system 124 are possible. The lens may include an f-theta lens, which may be configured to apply field correction so as to recover a flat field condition. In some embodiments, the lens may include an optical material substantially transmissive to light at both the excitation wavelength and the ablation wavelength. For example, the lens may include zinc selenide (ZnSe). The lens may include additional or alternative optical materials.

Figure 2:
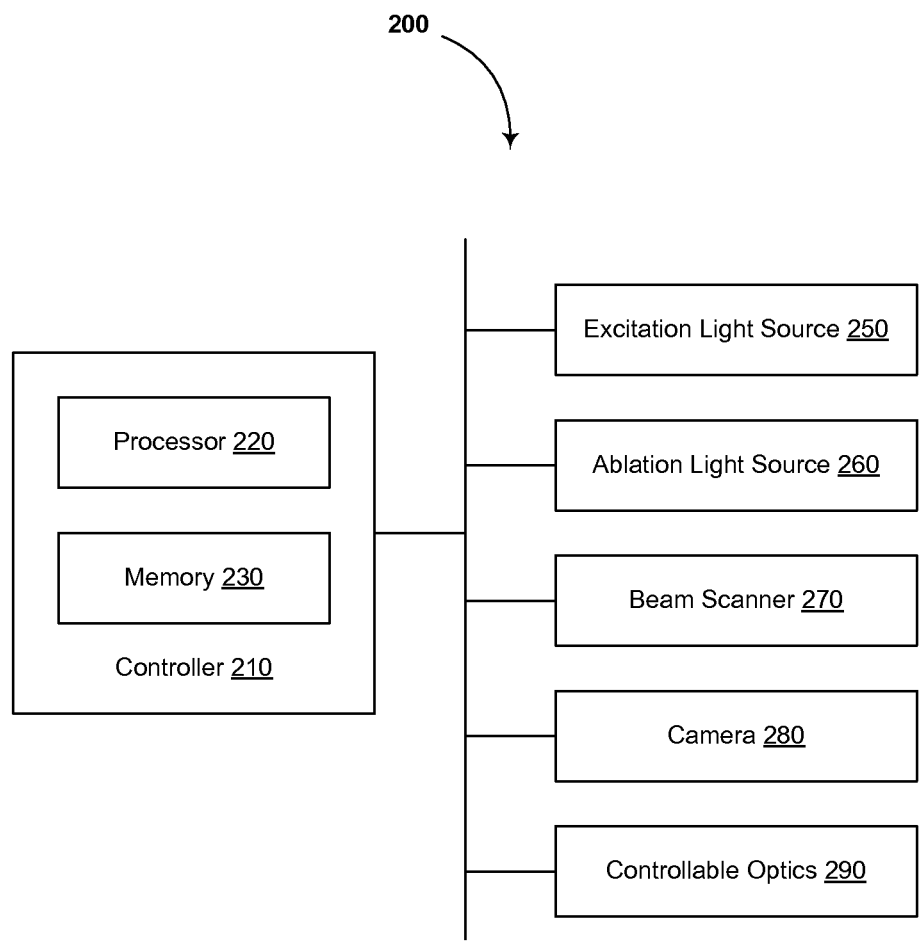
FIG. 2 illustrates a schematic block diagram of an apparatus, according to an example embodiment.

FIG. 2 illustrates a schematic block diagram of an apparatus 200, according to an embodiment. Elements of apparatus 200 may be similar or identical to elements of apparatus 100 as described and illustrated in reference to FIGS. 1A-C. A controller 210 may include a processor 220 and a memory 230. Memory 230 may be non-transitory in nature. The controller 210 may include a mobile device, a laptop computer, or another computing device. The controller 210 may include one or more computers. The computers need not be collocated, but may be distributed, for example as part of a cloud server network.

Program instructions may be stored in memory 230 and may be executable by processor 220. Such program instructions may include instructions that carry out or cause the elements of the methods illustrated and described in reference to FIGS. 3 and 4. Namely, the program instructions may include causing an excitation light source to produce excitation light. The excitation light includes light having a wavelength that corresponds to an excitation wavelength of a fluorophore. The fluorophore is configured to emit emission light at an emission wavelength in response to receiving light at the excitation wavelength. The program instructions may include causing a beam scanner to direct the excitation light towards a particular tissue location. The beam scanner is operable to direct the excitation light toward any of a plurality of tissue locations. The program instructions may further include causing a camera to capture at least the particular tissue location. The camera is configured to detect the emission light emitted by the fluorophore. The program instructions may also include determining a fluorescence condition based on the image indicating emission light at the emission wavelength at the particular tissue location. The program instructions may additionally include responsive to the fluorescence condition, causing an ablation light source to produce ablation light and causing the beam scanner to direct the ablation light towards the particular tissue location. The ablation light source and the excitation light source are optically coupled to a beam combiner. The beam combiner is optically coupled to the beam scanner. Other program instructions are possible to carry out or cause actions described elsewhere herein.

Apparatus 200 may further include an excitation light source 250, an ablation light source 260, a beam scanner 270, a camera 280, and optional controllable optics 290. The controller 210 may be able to communicate to each of the other elements of the apparatus 200 via a communication bus. Alternatively or additionally, controller 210 may be able to communicate with one or more of the other elements of apparatus 200 via direct wired and/or wireless communication links.

As described herein, controller 210 may control and/or adjust parameters associated with one or more of the other elements of apparatus 200. For example, controller 210 may cause the excitation light source 250 to produce excitation light. Furthermore, controller 210 may cause beam scanner 270 to direct excitation light towards a particular tissue location among a plurality of tissue locations. Controller 210 may additionally cause the camera 280 to capture an image of a field of view that includes at least the particular tissue location. In some embodiments, controller 210 may control other aspects of camera 280. For example, controller 210 may adjust the shutter speed or integration time, sensitivity (e.g. ISO), aperture, white balance, or other aspects of camera 280.

Controller 210 may determine that the image indicates light at an emission wavelength of a fluorophore at the particular tissue location. For example, controller 210 may analyze the image. The analysis may indicate that emission light at an expected emission wavelength is greater than a predetermined threshold (e.g. a minimum intensity). Under such conditions, the controller 210 may determine a fluorescence condition.

In response to determining the fluorescence condition, the controller 210 may cause the ablation light source 260 to produce ablation light and cause the beam scanner 270 to direct the ablation light towards the particular tissue location.

Controller 210 may also optionally adjust or control various controllable optics 290. Controllable optics 290 may include optical components that are configured to focus, direct, steer, adjust, reflect, or attenuate/absorb the light in apparatus 200. For example, controller 210 may control a lens so as to obtain optimal or proper focus of excitation light and/or ablation light at the particular tissue location. Controller 210 may control other elements of apparatus 200 as well. For instance, controller 210 may adjust neutral density filters, spectral filters, shutters, apertures, beam stops, etc. associated with apparatus 200.

Controller 210 may be configured to determine a topographical map of at least the particular tissue location based on a location of the camera, a location of the exit aperture, and an angle of the excitation light with respect to the particular tissue location being illuminated by the excitation light. That is, the controller 210 may illuminate the particular tissue location with the excitation light source 250 and capture an image using the camera 280. The captured image may include the particular tissue location. Because respective locations of the exit aperture and the camera 280, as well as an angle of excitation light with respect to the particular tissue location are known, it is possible to calculate a focal distance (e.g. distance to target) with respect to the particular tissue location. In some embodiments, a triangulation method may be used to determine the focal length or distance to the particular tissue location. Other algorithms or methods may be used within the scope of this disclosure.

Controller 210 may be further configured to cause the camera to, while the ablation light source is producing ablation light, capture a second image of at least the particular tissue location and control the ablation light source based on the second image. Further images are possible as well. In one embodiment, the particular tissue location may be imaged subsequent or concurrent to providing ablation light to the particular tissue location. In some embodiments, a plurality of images may be captured before and during tissue ablation. Such subsequent imaging may help users remove the desired tissue while reducing a surgical margin or removal of undesired tissue.

Method Examples

Figure 3:
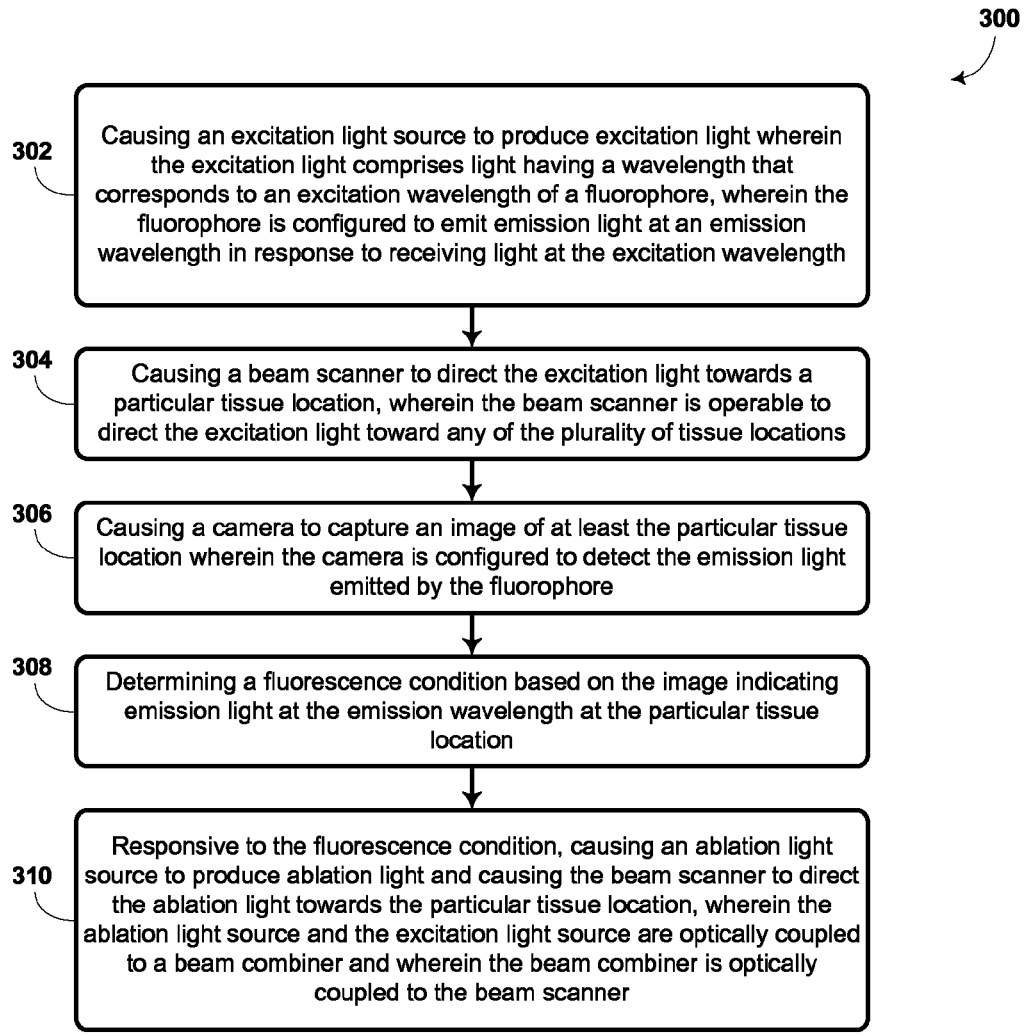
FIG. 3 illustrates a method, according to an example embodiment.

FIG. 3 illustrates a method 300, according to an embodiment. The method 300 includes blocks that may be carried out in any order. Furthermore, various blocks may be added to or subtracted from method 300 within the intended scope of this disclosure. The method 300 may correspond to steps that may be carried out using apparatus 100 or apparatus 200, as illustrated and described in reference to FIGS. 1A-C and FIG. 2.

Block 302 includes causing an excitation light source to produce excitation light. The excitation light may include light having a wavelength that corresponds to an excitation wavelength of a fluorophore. The fluorophore may be configured to emit emission light at an emission wavelength in response to receiving light at the excitation wavelength.

Block 304 includes causing a beam scanner to direct the excitation light towards a particular tissue location from a plurality of tissue locations.

Block 306 includes causing a camera to capture an image of at least the particular tissue location. The camera is configured to detect the emission light emitted by the fluorophore.

Block 308 includes determining a fluorescence condition based on the image indicating emission light at the emission wavelength at the particular tissue location. Determining the fluorescence condition may include an image analysis of the captured image. The image analysis may include, but is not limited to, spectral analysis, color mapping, color recognition, color matching, or other image analysis methods. In some embodiments, a threshold may be used to indicate, for example, a minimum intensity or a minimum luminosity at the emission wavelength. The threshold may be applied to a particular pixel, image area, or set of pixels within the image. In one embodiment, the fluorescence condition may be determined when, upon image analysis, a set of pixels from the image indicate an average intensity at the emission wavelength that is above the threshold. Other ways of determining the fluorescence condition are possible and considered within the scope of the present disclosure. Some embodiments may include determining the fluorescence condition based on the image indicating emission light from specific cells or tissue regions, which may be desired to be removed. For example, one or more fluorophores may be introduced into tissue. The one or more fluorophores may bind, associate, or otherwise become collocated with specific cells or tissues. As contemplated herein, emission from the one or more fluorophores may indicate the specific cells or tissues to be removed and/or ablated.

Block 310 includes responsive to the fluorescence condition, causing an ablation light source to produce ablation light and causing the beam scanner to direct the ablation light towards the particular tissue location. The ablation light source and the excitation light source are optically coupled to a beam combiner and the beam combiner is optically coupled to the beam scanner. As described above, the beam scanner may include a dual galvanometer. Other types of beam scanners are contemplated within the scope of this disclosure. For example, other beam steering devices configured to direct the excitation light and the ablation light are possible.

Optionally, the method may include causing the camera to capture a second image while the ablation light source is producing ablation light. In some embodiments, after determining the fluorescence condition, the camera may capture one or more subsequent images. The subsequent images may be captured while the ablation light source is producing ablation light. In such scenarios, the subsequent images may be used to determine a current fluorescence condition. In other words, the subsequent images may include further indication of fluorescence at the particular tissue location or lack thereof. With such information, a controller, processor, or other device may cause the ablation light source to continue producing ablation light, e.g. in the case that fluorescence is indicated in the subsequent images. Furthermore, the controller, processor or other device may cause the ablation light source to stop producing or reduce the ablation light in the case that fluorescence is not indicated, or indicated at an intensity below a predetermined threshold, in the subsequent images.

Figure 4:
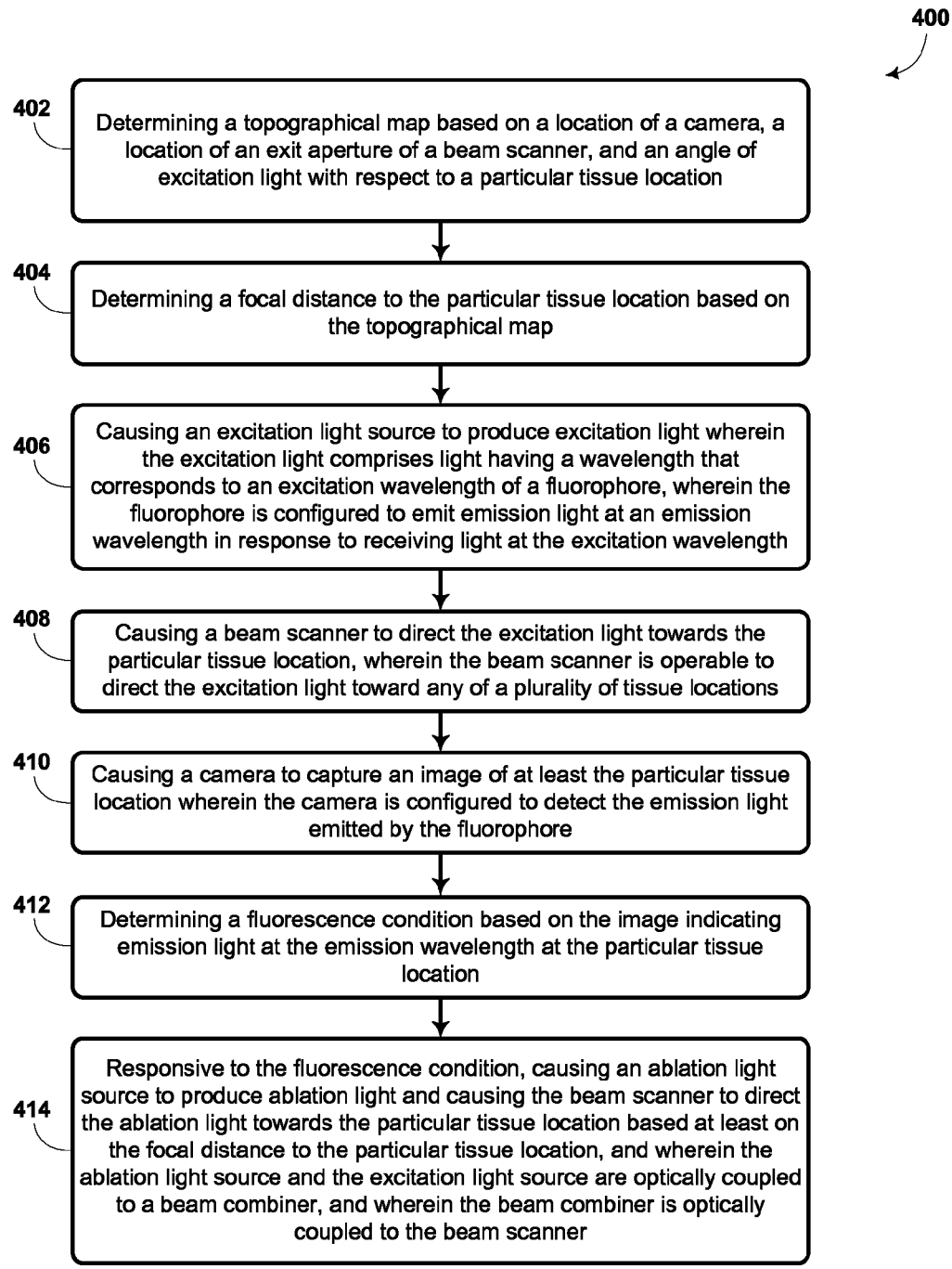
FIG. 4 illustrates a method, according to an example embodiment.

FIG. 4 illustrates a method 400, according to an embodiment. The method 400 includes blocks that may be carried out in any order. Furthermore, various blocks may be added to or subtracted from method 400 within the intended scope of this disclosure. The method 400 may correspond to steps that may be carried out using some or all of the elements of apparatus 100 or apparatus 200, as illustrated and described in reference to FIGS. 1A-C and FIG. 2.

Block 402 includes determining a topographical map based on a location of a camera, a location of an exit aperture of a beam scanner, and an angle of excitation light with respect to a particular tissue location from a plurality of tissue locations.

Block 404 includes determining a focal distance to the particular tissue location based on the topographical map.

Block 406 includes causing an excitation light source to produce excitation light. The excitation light may include light having a wavelength that corresponds to an excitation wavelength of a fluorophore. The fluorophore may be configured to emit emission light at an emission wavelength in response to receiving light at the excitation wavelength.

Block 408 includes causing a beam scanner to direct the excitation light towards a particular tissue location from a plurality of tissue locations.

Block 410 includes causing a camera to capture an image of at least the particular tissue location. The camera is configured to detect the emission light emitted by the fluorophore.

Block 412 includes determining a fluorescence condition based on the image indicating emission light at the emission wavelength at the particular tissue location.

Block 414 includes responsive to the fluorescence condition, causing an ablation light source to produce ablation light and causing the beam scanner to direct the ablation light towards the particular tissue location based at least on the focal distance to the particular tissue location. The ablation light source and the excitation light source are optically coupled to a beam combiner and the beam combiner is optically coupled to the beam scanner.

Topography Mapping Examples

Figure 5:
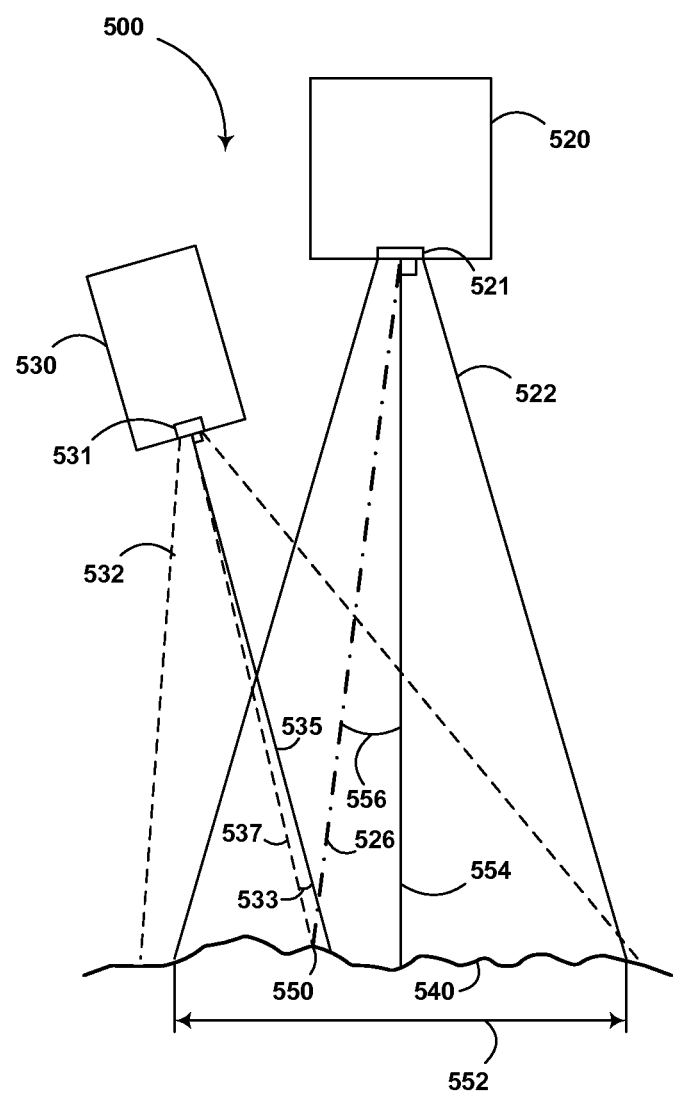
FIG. 5 illustrates a topography mapping scenario, according to an example embodiment.

FIG. 5 illustrates a topography mapping scenario 500, according to an embodiment. Topography mapping scenario 500 may include similar or identical elements as described elsewhere herein. For example, topography mapping scenario 500 may include elements from apparatus 100 and apparatus 200 as illustrated and described in reference to FIGS. 1A-C and FIG. 2. Furthermore, topography mapping scenario 500 may relate to various blocks from methods described herein, for example, blocks 402, 404, and 414 of method 400.

The topography mapping scenario 500 may include a beam scanner 520, a camera 530, and tissue 540. Beam scanner 520 may be operable to direct incident light 526 within a scanning range 522 toward any of a plurality of tissue locations 552. Incident light 526 may include excitation light and/or ablation light as described above and illustrated with respect to FIGS. 1A-C. Incident light 526 may form an incident angle 556 with respect to an axial beam scanner reference 554. Camera 530 may be configured to capture an image of the particular tissue location 550 within a field of view 532. Additionally, an image angle 533 may be provided between an axial camera reference 535 and a line 537 between the camera aperture 531 and the particular tissue location 550. Furthermore, a location of the camera 530, such as a location of the camera aperture 531 may be known with respect to an exit aperture 521 of the beam scanner 520. By knowing incident angle 556 and the location of the camera 530 with respect to exit aperture 521, a triangulation method may be used to determine a distance to target or a focal length.

Additionally or alternatively, the triangulation method may be carried out by knowing the distance between two points and the respective angles between the cord between the two points and a third point. In other words, the triangulation method may also be carried out in situations where a distance between the exit aperture 521 and the camera aperture 531 is known and the incident angle 556 and the image angle 533 are known. Other ways of carrying out the triangulation method so as to produce a topographic map of at least the particular tissue location are possible.

In some embodiments, other methods may provide or determine a topographic map of a tissue region or a plurality of tissue locations 540. The topographic map may be used to determine, for example, a distance to a particular tissue location. The distance to a particular tissue location may represent a focal distance. Based on information from the topographic map, a controller, such as controller 210 may be operable to adjust or otherwise control other elements of apparatus 100 and apparatus 200. For example, based on a focal distance to a particular tissue location, the controller 210 may be configured to adjust a focus of the excitation light source and/or the ablation light source, as described above.

The particular arrangements shown in the Figures should not be viewed as limiting. It should be understood that other embodiments may include more or less of each element shown in a given Figure. Further, some of the illustrated elements may be combined or omitted. Yet further, an illustrative embodiment may include elements that are not illustrated in the Figures.

While various examples and embodiments have been disclosed, other examples and embodiments will be apparent to those skilled in the art. The various disclosed examples and embodiments are for purposes of illustration and are not intended to be limiting, with the true scope and spirit being indicated by the following claims.

What is claimed is:

1. An apparatus comprising:
an excitation light source configured to produce excitation light wherein the excitation light comprises light having a wavelength that corresponds to an excitation wavelength of a fluorophore, wherein the fluorophore is configured to emit emission light at an emission wavelength in response to receiving light at the excitation wavelength;

an ablation light source configured to produce ablation light wherein the ablation light is configured to ablate tissue;

a beam combiner optically coupled to the excitation light source and the ablation light source;

a camera configured to detect the emission light emitted by the fluorophore; and a controller, wherein the controller comprises a computer programmed to carry out instructions, the instructions comprising:

causing the excitation light source to produce excitation light;

causing the camera to capture an image of at least a particular tissue location;

determining a topographical map of at least the particular tissue location based on a location of the camera and an angle of the excitation light with respect to the particular tissue location from the plurality of tissue locations;

determining a fluorescence condition based on the image indicating emission light at the emission wavelength at the particular tissue location; and responsive to the fluorescence condition, causing the ablation light source to produce ablation light.

2. The apparatus of claim 1 further comprising:
a beam scanner optically coupled to the beam combiner and operable to direct the excitation light and the ablation light toward any of a plurality of tissue locations, wherein the plurality of tissue locations comprise the particular tissue location;
wherein the instructions further comprise:
causing the beam scanner to direct the excitation light towards the particular tissue location.

3. The apparatus of claim 2 further comprising an optical system optically coupled to the beam scanner, wherein the optical system comprises an exit aperture and a lens, and wherein the controller is further configured to determine a focal distance to the particular tissue location based on the topographical map, wherein the ablation light source is operated to produce the ablation light and the beam scanner is operated to direct the ablation light towards the particular tissue location based on the determined focal distance such that the ablation light is provided in-focus to the particular tissue location.

4. The apparatus of claim 3 wherein the lens comprises zinc selenide (ZnSe).

5. The apparatus of claim 3 wherein the optical system is configured to correct field curvature.

6. The apparatus of claim 2, wherein the beam scanner comprises a dual galvanometer scanning mirror operable to deflect the excitation light and the ablation light within a deflection range that encompasses the plurality of tissue locations.

7. The apparatus of claim 2 wherein the controller is further configured to: while the ablation light source is producing ablation light, cause the camera to capture a second image of at least the particular tissue location and control the ablation light source based on the second image.

8. The apparatus of claim 2 further comprising a beam delivery system optically coupled to the beam combiner and the beam scanner and wherein the beam delivery system comprises an optical fiber.

9. The apparatus of claim 1 wherein the beam combiner comprises a fiber optic y-coupler.

10. The apparatus of claim 1 wherein the excitation light source comprises a laser, and wherein the excitation wavelength is between 380 nm and 1.4 microns.

11. The apparatus of claim 1 wherein the ablation light source comprises a carbon dioxide ($CO_2$) laser configured to produce the ablation light at an ablation wavelength between 1.4 microns and 12 microns.

12. The apparatus of claim 1 wherein the beam combiner comprises a dichroic material.

13. A method comprising
causing an excitation light source to produce excitation light wherein the excitation light comprises light having a wavelength that corresponds to an excitation wavelength of a fluorophore, wherein the fluorophore is configured to emit emission light at an emission wavelength in response to receiving light at the excitation wavelength;

causing a beam scanner to direct the excitation light towards a particular tissue location, wherein the beam scanner is operable to direct the excitation light toward any of a plurality of tissue locations;

causing a camera to capture an image of at least the particular tissue location wherein the camera is configured to detect the emission light emitted by the fluorophore;

determining a topographical map of at least the particular tissue location based on a location of the camera and an angle of the excitation light with respect to the particular tissue location from the plurality of tissue locations;

determining a fluorescence condition based on the image indicating emission light at the emission wavelength at the particular tissue location; and responsive to the fluorescence condition, causing an ablation light source to produce ablation light and causing the beam scanner to direct the ablation light towards the particular tissue location, wherein the ablation light source and the excitation light source are optically coupled to a beam combiner and wherein the beam combiner is optically coupled to the beam scanner.

14. The method of claim 13 wherein the beam scanner comprises an optical system, and wherein the optical system comprises an exit aperture and a lens.

15. The method of claim 13 further comprising determining a focal distance to the particular tissue location based on the topographical map, wherein the ablation light source is operated to produce the ablation light and the beam scanner is operated to direct the ablation light towards the particular tissue location based on the determined focal distance such that the ablation light is provided in-focus to the particular tissue location.

16. The method of claim 13 wherein the beam scanner comprises a dual galvanometer scanning mirror operable to deflect the excitation light and the ablation light within a deflection range that encompasses the plurality of tissue locations.

17. The method of claim 13 further comprising while the ablation light source is producing ablation light, causing the camera to capture a second image of at least the particular tissue location and controlling the ablation light source based on the second image.

18. The method of claim 13 wherein the excitation light further comprises light having a second wavelength that corresponds to a second excitation wavelength of a second fluorophore, wherein the fluorophore is configured to emit second emission light at a second emission wavelength in response to receiving light at the second excitation wavelength, and determining the fluorescence condition based further on the image indicating second emission light at the second emission wavelength at the particular tissue location being below a threshold.

19. A method comprising:
- determining a topographical map based on a location of a camera, a location of an exit aperture of a beam scanner, and an angle of excitation light with respect to a particular tissue location of a plurality of tissue locations;
- determining a focal distance to the particular tissue location based on the topographical map;
- causing an excitation light source to produce excitation light wherein the excitation light comprises light having a wavelength that corresponds to an excitation wavelength of a fluorophore, wherein the fluorophore is configured to emit emission light at an emission wavelength in response to receiving light at the excitation wavelength;
- causing a beam scanner to direct the excitation light towards a particular tissue location, wherein the beam scanner is operable to direct the excitation light toward any of a plurality of tissue locations;
- causing a camera to capture an image of at least the particular tissue location wherein the camera is configured to detect the emission light emitted by the fluorophore;
- determining a fluorescence condition based on the image indicating emission light at the emission wavelength at the particular tissue location; and
- responsive to the fluorescence condition, causing an ablation light source to produce ablation light and causing the beam scanner to direct the ablation light towards the particular tissue location based at least on the focal distance to the particular tissue location, and wherein the ablation light source and the excitation light source are optically coupled to a beam combiner, and wherein the beam combiner is optically coupled to the beam scanner.

20. The method of claim 19 further comprising while the ablation light source is producing ablation light, causing the camera to capture a second image of at least the particular tissue location and controlling the ablation light source based on the second image.

* * * * *